United States Patent [19]

Burns et al.

[11] Patent Number: 5,101,014

[45] Date of Patent: Mar. 31, 1992

[54] PROCESS FOR THE PURIFICATION OF A 69,000 DA OUTER MEMBRANE PROTEIN OF BORDETELLA PERTUSSIS

[75] Inventors: Drusilla L. Burns, Washington, D.C.; Michael J. Brennan, Kensington, Md.; Jeanine L. Gould-Kostka, Rockville, Md.; Charles R. Manclark, Rockville, Md.

[73] Assignee: The Government of the United States of America, Washington, D.C.

[21] Appl. No.: 308,864

[22] Filed: Feb. 10, 1989

[51] Int. Cl.$^5$ .................. C07K 15/04; C07K 15/14; C07K 3/18; C07K 3/28

[52] U.S. Cl. .................. 530/350; 530/395; 530/806; 530/416; 530/412; 530/417; 530/413

[58] Field of Search ............... 530/416, 417, 412, 413, 530/350, 395, 806

[56] References Cited

U.S. PATENT DOCUMENTS 3,959,251  5/1976  Porath .

OTHER PUBLICATIONS

Craig et al., 1988, J. Gen. Microbiol., 134:2201-2211.
Olancher et al., 1990, Microbiol. Pathogenesis 8:37-45.
Weiss et al., 1983, Infection and Immunity 42(1):33-41.
Weiss et al., 1986, Ann. Rev. Microbiol. 40:661-686.
Collier et al., 1977, J. Infect. Dis. vol. 136 Supplement pp. 5196-5203.
Urisu et al., 1985, Proc. 4th Int. Symp. on Pertussis, Joint IABS/WHO Meet, Geneva Switzerland, 61:205-214.
Sultzer et al., 1985, Proc. 4th Int Symys. on Pertussis, Joint IABS/WHO Meet., Geneva Switzerland, 61:225-232.
Ashworth et al., 1985, Proc. 4th Int. Symp. on Pertussis, Joint IABS/WHO Meet., Geneva Switzerland, 61:143-151.
Goldman et al., 1985, Proc. 4th Int. Symp. on Pertussis, Joint IABS/WHO Meet., Geneva Switzerland, 61:103-111.
Muse et al., 1978, Proc. 3rd Int. Symp. on Pertussis, Joint IABS/NIAID, Bethesda, Maryland, U.S.A. pp. 41-50.
Manclark et al., 1986, Manual of Clinical Laboratory Immunology 3rd Edition, (eds.) Rose et al., Amer. Soc. Microbiol., Washington, D.C.pp. 388-394.
Brennan et al., 1988 Infection and Immunity 56(12):3189-3195.
Li et al., 1988, Infection and Immunity 56(12):3184-3188.
Li et al., 1988, Infection and Immunity 56(3):699-702.
McCormick, 1987, Biol. Technology 5:246, 249 and 250.
Montaraz et al., 1985, *Infection and Immunity* 47(3):744-751.
Novotny et al., 1985 *Infection and Immunity* 50(1): 199-206.
Scoper, 1987, *Protein Purification:Principles and Practice*, Springer-Verlag, New York, pp. 104-107, 120-125, 141-157.
Apr. 1987 Bio-Rad. Catalog, Price List M, p. 83.
Sekura et al., 1983, *J. of Biol. Chem.* 258(23): 14647-14651.

(List continued on next page.)

*Primary Examiner*—Margaret Moskowitz
*Assistant Examiner*—Keith C. Furman
*Attorney, Agent, or Firm*—Cushman, Darby & Cushman

[57] ABSTRACT

The present invention comprises a method for the purification of the 69 kDa outer membrane protein of *Bordetella pertussis* and the protein purified therewith. A preferred embodiment comprises the purification of the 69 kDa protein from *Bordetella pertussis* strain Bp 353. The present process is advantageous in that it does not require or involve the use of biologics (such as monoclonal antibodies) and therefore simplifies the purification procedure and makes the resulting purified protein particularly advantageous for inclusion in acellular vaccines.

9 Claims, 1 Drawing Sheet

OTHER PUBLICATIONS

Charles, et al., Molecular Cloning and Characterization of Protective Outer Membrane Protein p. 69 From Bordetella Pertussis; Proc. Natl. Acad. Sci. USA, 86:3554–3558 (1989).

Dean, et al., Protein Purification Using Immobilised Triazine Dyes; J. Chromatography, 165:301–319 (1979).

Hanggi, et al., Analytical Evaluation of the Purity of Commercial Preparations of Cibracron Blue F3GA and Related Dyes; Anal. Biochem., 149:91–104 (1985).

Burgett, et al., Cibracron Blue F3GA Affinity Chromatography; American Laboratory, (May, 1977) First page of Article.

Red Sepharose CL-68 for Affinity Chromatography; and Attached Materials Published by Pharmacia Fine Chemicals.

Affinity Chromatography—Principles & Methods (cover page and p. 74).

Shattuck, et al., "Purification and Characterization of a Calmodulin-Sensitive Adenylate Cyclase from Bordetella Pertussis", Biochemistry 1985, vol. 24, pp. 6356–6362.

Kessin, et al., "Secreted Adenylate Cyclase of Bordetella Pertussis: Calmodulin Requirements and Partial Purification of Two Forms", Journal of Bacteriology, Apr. 1986, vol. 166, No. 1, pp. 290–296.

Hewelett, et al., "Adenylate Cyclase Toxin from Bordetella Pertussis", The Journal of Biological Chemistry, vol. 264, No 32, Nov. 15, 1989, pp. 19379–19384.

Friedman, "Bordetella Pertussis Adenylate Cyclase: Isolation and Purification by Calmodulin-Sepharose 4B Chromatography," Infection and Immunity, vol. 55, No. 1, Jan. 1987, pp. 129–134.

PROCESS FOR THE PURIFICATION OF A 69,000 DA OUTER MEMBRANE PROTEIN OF BORDETELLA PERTUSSIS

BACKGROUND OF INVENTION

*Bordetella pertussis* is the bacterial pathogen responsible for whooping cough in humans. Serotype markers for the bacterium have been defined by the ability of strain-specific polyclonal antisera to agglutinate the bacteria. E. K. Andersen first identified five distinctive agglutinogen factors in 1953 (Acta Pathol. Microbiol. Scand. 33:202–224 (1953)), and Eldering et al. subsequently added agglutinogen factor 6 (J. Bacteriol. 74:133–136 (1957)). Following whooping cough outbreaks, it has been noted that there tends to be a prevalence of certain *Bordetella pertussis* serotypes, and the serum agglutinin titers of human vaccinees appear to correlate with clinical protection from pertussis.

Some of the agglutinogen factors have been defined, for instance, the expression of lipooligosaccharide A (LOS A) by *Bordetella pertussis* cells appears to correlate with the presence of the serotype 1 agglutinogen factor. Likewise, serotype 2 and 6 agglutinogens have been found to correspond to fimbriae while the serotype 3 agglutinogen factor is composed of both fimbriae and a 69 kDa outer membrane protein.

The present inventors describe herein as an object of their invention, a new method for the isolation and purification of cell proteins, specifically the nonfimbrial 69 kDa outer membrane protein of *Bordetella pertussis*. The protein purified by the method of the present invention is useful in the preparation of *Bordetella pertussis* hybridomas and serotype-specific monoclonal antibodies (Mabs) thereto. The protein can also be advantageously utilized for a wide range of diagnostic, manufacturing and research purposes including, but not limited to inclusion in acellular pertussis vaccines.

Two groups have previously published purification procedures for the *Bordetella pertussis* 69 kDa protein or for the related 68 kDa protein from *Bordetella pertussis*, which is antigenically similar to the 69 kDa protein.

The most recently disclosed method is that described by Brennan et al. (Infect. Immun. 56:3189–3195 (1988)). In summary it is a multi-step procedure, the first step being the purification of the protein from the bacteria by heating the bacterial cells at 60° C. for 1 hour. The resulting extract is then applied to a fetuin-Sepharose 4B column, followed by chromatography of the fractions containing the 69,000 Da protein on an immunoaffinity column in which a monoclonal antibody specific for the 69,000 Da protein was linked to agarose. The 69,000 Da protein was then eluted from the column with 6M urea.

The second purification procedure was disclosed by Novotny et al. (Infect. Immun. 50:199–206 (1985)) and involves as a first step the preparation of an acid glycine hydrolyzate of the bacteria. The resulting extract was dialyzed versus 0.025M Tris, pH 8.8, containing 0.035M NaCl, then chromatographed on DEAE-Trisacryl. Material which was not retained by the column was subjected to isoelectrofocusing. Pooled eluants from zones of pH 7.5 to 7.0 were applied to an immunoaffinity column in which a monoclonal antibody specific for the 68,000 Da *Bordetella bronchiseptica* protein was linked to Sepharose CL-6B. Sepharose CL is prepared by cross-linking agrose with 2,3-dibromopropanol and desulfating the resulting gel by alkaline hydrolysis under reducing conditions. The protein was eluted from the column with buffer containing 6M urea.

The invention described in the present application differs from the above purification schemes in that the procedures are substantially different and do not require the use of an immunoaffinity column and monoclonal antibodies which is advantageous, for the production of monoclonal antibodies is both time consuming and expensive. Therefore, this method is quicker and cheaper than methods previously disclosed.

In addition to the above, the process of the present invention also allows for easy scale-up. This is advantageous since large-scale purification processes are needed to produce sufficient quantities of proteins such as the 69,000 Da protein for use in vaccines. Similarly, the present process does not require or involve additional biologics (such as monoclonal antibodies), the use of which should be avoided, if possible, when producing proteins for inclusion in vaccines.

Further objects and advantages of the invention will become apparent from the following description.

SUMMARY OF INVENTION

Virulent strains of *Bordetella pertussis* produce a 69,000 Da outer membrane protein which is antigenically related to proteins produced by other Bordetella species. Antibodies to this protein agglutinate certain *Bordetella pertussis* strains. The protein has been shown to be a protective antigen in certain animal models and may be suitable candidate for inclusion in acellular pertussis vaccines.

Prior to the present invention, protocols for the purification of bacterial proteins were complicated by the use of monoclonal antibody affinity columns which make the protein purification process a lengthy and expensive procedure. The present inventors have devised a purification scheme which obviates the need for this affinity purification step. According to the present invention, a heat extract of *Bordetella pertussis* cells was prepared using essentially the method of Brennan et al., supra, specifically incorporated herein by reference.

The procedure of the present invention is simple, and is believed to be suitable for use with all 69 kDa producing strains of *Bordetella pertussis*. Suitable strains for use herein are phase I (virulent) strains which include, but are not limited to Bp 353 114, 460 and 150. In a preferred embodiment of the invention, the 69 kDa protein of strain Bp 353 has been purified as disclosed.

The present invention is illustrated in more detail below in FIG. 1 and in the detailed description of the invention. The invention is illustrated by way of example which is to be viewed in a non-limitative manner.

DETAILED DESCRIPTION OF INVENTION

Figure 1:
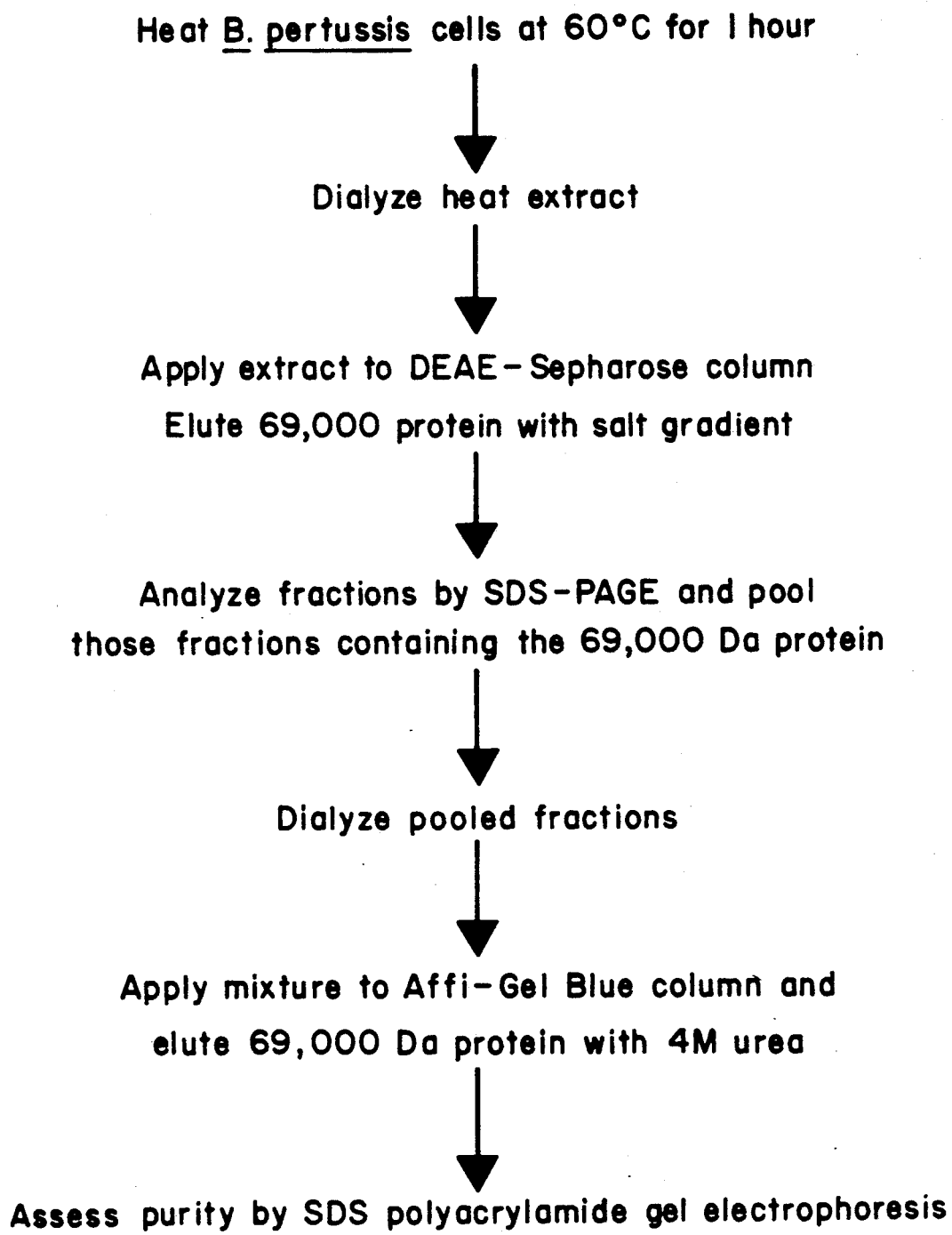
FIG. 1. Schematic of the protein purification of the 69,000 Da outer membrane cell protein of *Bordetella pertussis*.

A novel procedure for the purification of the 69,000 Da protein of *Bordetella pertussis* which does not require an immunoaffinity step is described below and in Example 1 which is outlined in FIG. 1. The process generally comprises the steps of:

a) preparing a protein extract containing the 69 kDa protein of *Bordetella pertussis* using, for example, the method of Brennan et al., as modified;

b) applying the protein extract to an anion-exchange column such as DEAE-sepharose (Diethylaminoethyl-Sepharose) (Pharmacia, Sweden);

c) separating the 69 kDa protein from the extract and eluting it from the column generally with a linear salt gradient although, the specific conditions required for the elution of the 69 kDa protein can be more narrowly determined and the requirement for or range of the gradient negated or limited;

d) pooling those eluate fractions containing the 69 kDa protein. This step achieves the initial purification of the 69 kDa protein from other proteins in the extract;

e) applying the pooled fractions on an affinity column containing a protein-specific binding medium such as AFFI-GEL BLUE (beaded crosslinked agarose gel with covalently attached Cibracron Blue F3GA dye) (Bio-Rad, Richmond, Calif.), a matrix which binds to the 69 kDa protein of *Bordetella pertussis*, as well as others, and permits the elution of the 69 kDa protein from the column with urea, thereby separating it from contaminating proteins;

f) eluting the 69 kDa protein from the column and collecting the purified protein eluate. When using Affi-Gel Blue, urea is employed as the protein eluant. While urea ranging from 1M to 8M was tested for use herein, urea of about 4M was found to achieve optimum separation and purification of the 69 kDa protein from remaining protein on the column. Higher concentrations of urea tended to elute contaminating proteins along with the 69 kDa protein, while lower concentrations were insufficient to completely elute the 69 kDa protein.

EXAMPLE 1

A protein extract of *Bordetella pertussis* strain Bp 353, a Tn 5 insertion mutant provided by Dr. Alison Weiss, Medical College of Virginia, Richmond, Va., was prepared by a modified method of Brennan et al., which method comprised the incubation of *Bordetella pertussis* cells suspended in a Tris-buffered saline solution (TBS; 0.01M Tris-HCl, pH 8.0, 0.15M NaCl) containing 0.002% Na azide and 1 mM phenylmethylsulfonylfluoride (PMSF) (Sigma, St. Louis, Mo.) at 60° C. for 1 hour (about $6\times10^{12}$ washed bacteria/30 ml buffer).

In this example, PMSF serves as a protease inhibitor which is used to alleviate protein breakdown during the purification process. Other protease inhibitors are known and may be used herein to achieve similar results. Likewise, the sodium azide serves as a bacterial growth inhibitor. As with the PMSF, other growth inhibitors are known and may be used to achieve similar results.

After heating, the cell solution was centrifuged twice at $4,000\times g$ (30 minutes each) in order to pellet the cell debris and to separate it from the supernatant which contains the 69 kDa protein. The cell debris was discarded and the supernatant was retained for further processing.

The supernatant was dialyzed against 0.25M Tris-HCl, pH 8.8, containing 1 mM PMSF (buffer A). This dialysis step served to remove small molecular weight impurities from the supernatant, as well as to change the salt concentration and pH of the solution, thereby preparing the solution for application onto an ion-exchange column for further purification. It should be clear that the pH and salt concentration of the dialysis buffer may be varied depending upon the specific ion-exchange media employed and the conditions required thereby.

The dialysate was applied to an ion-exchange column containing DEAE-SEPHAROSE (Pharmacia, Sweden) which had been equilibrated with buffer A. About 1.5 ml of DEAE-SEPHAROSE was used per mg of protein applied. It is believed, however, that this ratio may be conservative, and that significantly more protein could have been added before overloading of the column occurred.

The column was eluted using approximately 4 column volumes of a linear salt gradient of 0–0.12M NaCl in buffer A. The eluate fractions were collected, and a second elution of the column using about 1.5 column volumes of buffer A containing 0.2M NaCl was run in order to maximize protein recovery and to insure that all the 69 kDa protein had eluted from the column.

The eluate fractions were analyzed by sodium dodecyl sulfate-polyacrylamide gel electrophoresis (SDS-PAGE) to determine which fractions contained the 69 kDa protein. Those fractions were then pooled and dialyzed against 20 mM Tris-HCl, pH 7.4, containing 1 mM PMSF (buffer B).

As noted above, the dialysis step served to remove small molecular weight impurities from the pooled eluate, if any were present, but more importantly served to prepare the pooled protein for application onto an affinity column containing AFFI-GEL BLUE (beaded crosslinked agarose gel with covalently attached CIBRACRON BLUE F3GA dye). It is contemplated that other affinity columns containing protein-specific binding dyes other than AFFI-GEL BLUE such as BLUE SEPHAROSE (crosslinked agarose gel with CIBRACRON BLUE F3GA dye convalently attached or RED SEPHAROSE (crosslinked agarose covalently attached to the triazine dye, PROCION RED HE-3B; (Pharmacia, Sweden) could be used herein as well, in which case, the dialysis solution should be modified accordingly.

After dialysis, the dialysate was applied to an AFFI-GEL BLUE affinity column (about 1 ml AFFI-GEL BLUE per 50 ml dialysate) equilibrated with buffer B. The column was washed with about 6 column volumes of buffer B followed by about 6 column volumes of 0.5M potassium phosphate, pH 7.5, containing 75 mM NaCl, 0.5 mM ethylenediaminetetraacetic acid (EDTA), 0.5 mM PMSF and 0.1% Brij 35 (Polyoxyethylene 23:laurylether, 30% w/v) (Sigma Diagnostics, St. Louis, Mo.). This procedure removed trace contaminants such as non-69 kDa protein from the column.

The 69 kDa protein was then eluted from the column using about 4 column volumes of 10 mM Tris-HCl, pH 8.0, containing 4M urea, 0.15M NaCl, 1 mM EDTA, 1 mM PMSF and 0.1% Brij 35 (Sigma Diagnostics, St. Louis, Mo.) and collected. The eluate was analyzed with SDS-PAGE as discussed above.

The wash buffer employed in the AFFI-GEL BLUE chromatography employs Brij 35 as a detergent which serves to assist in the removal of contaminating proteins and LOS A from the affinity column. Other detergents are available which could also be used to achieve the present results. The urea in the eluant is believed to be primarily responsible for the elution of the 69 kDa protein from the AFFI-GEL BLUE column.

Using this procedure, the resulting 69,000 Da protein was found to bind the monoclonal antibody BPE3 (Brennan et al., supra) indicating that the purified protein was the same as that previously described.

We claim:

1. A process for the purification of the 69 kDA outer membrane protein of *Bordetella pertussis* comprising the steps of:
   a) preparing a protein extract containing said 69 kDa protein;
   b) applying said extract to an anion-exchange column under conditions sufficient to retain said 69 kDa protein on said column;
   c) separating said 69 kDa protein from said extract by eluting said column with an eluant and collecting the 69 kDa protein-containing eluate;
   d) applying said 69 kDa protein-containing eluate to a non-immunoaffinity column containing beaded cross-linked gel covalently attached to a protein-specific dye chosen from the group consisting of CIBRACRON BLUE F3GA dye, and the triazine dye, PROCION RED HE-3B.
   e) eluting the 69 kDa protein from said non-immuoaffinity column with an eluant, and collecting the 69 kDa protein-containing eluate.

2. The process of claim 1, step b), wherein said anion-exchange column comprises crosslinked agarose with covalently attached diethylaminoethyl groups, and said eluant of step c) comprises a linear salt gradient.

3. The method of claim 1, wherein said *Bordetella pertussis* is selected from phase I strains.

4. The method of claim 3, wherein said strains comprise Bp 363, 114, or 460.

5. The method of claim 4, wherein said *Bordetella pertussis* is strain Bp 353.

6. The process of claim 1 wherein the CIBRACRON BLUE F3GA dye covalently attached to the cross-linked gel is AFFI-GEL BLUE or BLUE SEPHAROSE, and wherein said eluant of step d) comprises about 4M urea.

7. The process of claim 1 wherein the PROCION RED HE-3B dye covalently attached to the cross-linked gel is RED SEPHAROSE.

8. The method of claim 4, wherein said strain is Bp 114.

9. The method of claim 4, wherein said strain is Bp 460.

* * * * *